US008500701B2

(12) United States Patent
Kirchhofer

(10) Patent No.: US 8,500,701 B2
(45) Date of Patent: Aug. 6, 2013

(54) ADMINISTERING DEVICE COMPRISING DISPLAY DRUM

(75) Inventor: Fritz Kirchhofer, Sumiswald (CH)

(73) Assignee: TecPharma Licensing AG, Burgdorft (CH)

( * ) Notice: Subject to any disclaimer, the term of this patent is extended or adjusted under 35 U.S.C. 154(b) by 833 days.

(21) Appl. No.: 11/843,108

(22) Filed: Aug. 22, 2007

(65) Prior Publication Data
US 2008/0077095 A1    Mar. 27, 2008

Related U.S. Application Data

(63) Continuation of application No. PCT/CH2006/000018, filed on Jan. 11, 2006.

(30) Foreign Application Priority Data

Feb. 23, 2005  (DE) .......................... 10 2005 008 280

(51) Int. Cl.
*A61M 5/00* (2006.01)

(52) U.S. Cl.
USPC ............ 604/211; 604/207; 604/208; 604/246

(58) Field of Classification Search
USPC ................ 604/181, 187, 207, 208, 209, 210, 604/211, 218, 223, 246
See application file for complete search history.

(56) References Cited

U.S. PATENT DOCUMENTS

| | | | | |
|---|---|---|---|---|
| 5,092,842 A | * | 3/1992 | Bechtold et al. | 604/135 |
| 5,320,609 A | | 6/1994 | Haber et al. | |
| 5,626,566 A | * | 5/1997 | Petersen et al. | 604/208 |
| 5,984,900 A | * | 11/1999 | Mikkelsen | 604/208 |
| 6,221,053 B1 | * | 4/2001 | Walters et al. | 604/211 |
| 6,235,004 B1 | * | 5/2001 | Steenfeldt-Jensen et al. | 604/207 |
| 7,112,187 B2 | * | 9/2006 | Karlsson | 604/187 |
| 7,291,132 B2 | * | 11/2007 | DeRuntz et al. | 604/207 |
| 2004/0019333 A1 | | 1/2004 | Graf et al. | |
| 2004/0210199 A1 | * | 10/2004 | Atterbury et al. | 604/224 |
| 2005/0033244 A1 | * | 2/2005 | Veasey et al. | 604/211 |
| 2007/0244436 A1 | * | 10/2007 | Saiki | 604/131 |

FOREIGN PATENT DOCUMENTS

| | | |
|---|---|---|
| DE | 10229138 A1 | 1/2004 |
| DE | 102 32 411 A1 | 2/2004 |
| DE | 20317377 U1 | 3/2005 |
| WO | 99/38554 A | 8/1999 |
| WO | 03/075985 A1 | 9/2003 |

* cited by examiner

*Primary Examiner* — Kevin C Sirmons
*Assistant Examiner* — Shefali Patel
(74) *Attorney, Agent, or Firm* — Dorsey & Whitney LLP; David E. Bruhn, Esq.

(57) ABSTRACT

A device for administering a product dose, the device including a display drum for displaying the product dose, a housing, a first conveying member moveable relative to the housing in a conveying direction, a second conveying member moveable relative to the housing in and counter to the conveying direction, the second conveying member in a first threaded engagement with the first conveying member while being rotationally movable relative to the housing and the first conveying member and being translationally movable relative to the first conveying member counter to the conveying direction, a metering apparatus by which the product dose can be adjusted and which encompasses the display drum, the display drum being rotationally movable relative to the housing while being translationally movable in and counter to the conveying direction in a second threaded engagement, and a coupling element which interconnects the first conveying member and the display drum in a torsion-resistant manner in a coupling engagement which is releasable by actuating the device for administering.

22 Claims, 3 Drawing Sheets

US 8,500,701 B2

ADMINISTERING DEVICE COMPRISING DISPLAY DRUM

CROSS-REFERENCE TO RELATED APPLICATIONS

This application is a continuation of International Application No. PCT/CH2006/000018 filed on Jan. 11, 2006, which claims priority to German Application No. DE 10 2005 008 280.7 filed on Feb. 23, 2005, the contents of both of which are incorporated in their entirety herein by reference.

BACKGROUND

The present invention relates to devices for injecting, infusing, delivering, dispensing or administering substances, and to methods of making and using such devices. More particularly, the present invention relates to a device for administering a fluid product or substance which can be a medicine, a diagnostic agent or a cosmetic product. In some preferred embodiments, the invention is used in self-administering, although it is not limited to self-administration use, but can also be used in administering by medically trained staff.

In therapies in which persons who are not medically trained administer an active agent, for example to themselves, the administering devices used have to be simple but still reliable to handle. In particular, it is necessary to ensure that in devices which allow selecting or setting the product dosage to be administered the dosage set is displayed accurately, conveniently and unequivocally. In diabetes therapy—a preferred area of use for the present invention—it should also be taken into account that the persons administering the insulin to themselves may be visually impaired and that the dosage set should therefore be particularly clearly and unambiguously legible on a dosage scale or display. It is conducive to good legibility if the dosage scale is disposed on a display drum which can be moved rotationally and translationally, since in this case, the dosage scale can extend along and in the rotational direction of the display drum.

Devices of the type mentioned are known for example from WO 99/38554 A1. Typically, the devices are complex and require rotational blocks which allow a rotational movement by a piston rod in one rotational direction but prevent it in the other, and which additionally have to be adjusted to torques which are to be transferred or can only just still be transferred.

A very simple device of the type mentioned is known from WO 03/075985 A1. As with the devices of WO 99/38554, however, it requires two spindle drives which are both formed to not be self-locking, such that when only a small dosage is set, only a short stroke of the display drum is provided.

SUMMARY

It is an object of the present invention to provide an administering device of the type mentioned above, i.e. an administering device comprising a display drum and spindle drives, which is designed simply and can therefore be provided cheaply, but can still be flexibly adapted to administering needs with respect to gearing up or also, as applicable, gearing down between a delivery stroke of a conveying means and an adjusting movement of the display drum, when the product dosage is being set.

In one embodiment, the present invention comprises a device for administering a product dose, the device including a display drum for displaying a product dose, a housing, a first conveying member moveable relative to the housing in a conveying direction, a second conveying member moveable relative to the housing in and counter to the conveying direction, the second conveying member in a first threaded engagement with the first conveying member while being rotationally movable relative to the housing and the first conveying member and being translationally movable relative to the first conveying member counter to the conveying direction, a metering apparatus by which a product dose can be adjusted and which encompasses the display drum, the display drum being rotationally movable relative to the housing while being translationally movable in and counter to the conveying direction in a second threaded engagement, and a coupling element which interconnects the second conveying member and the display drum in a torsion-resistant manner in a coupling engagement which is releasable by actuating the administering device.

In one embodiment, the present invention comprises a device for administering a fluid product which comprises a casing comprising a receptacle for the product, a conveying means for conveying the product and a dosing means for setting a product dosage to be administered and displaying the product dosage set. The casing forms a receptacle for the product, in some preferred embodiments in the form of a receptacle for a container which is filled with the product. In principle, however, the receptacle could also itself directly form the product container. The conveying means comprises a first conveying member which can be moved in a conveying direction relative to the casing to deliver the a selected product dosage in a conveying stroke which is pre-set in accordance with the product dosage. In some embodiments, the conveying stroke is a translational movement by the first conveying member in the conveying direction, e.g. a linear movement along a conveying axis. The first conveying member can be formed as a piston rod which, in such an embodiment, is connected to a piston of the conveying means, for example formed in one piece with the piston, screwed or latched to the piston, or pressing loosely against a rear side of the piston during the conveying stroke. The conveying means also comprises a second conveying member which is in a first threaded engagement with the first conveying member, in which it can be rotated relative to the first conveying member and the casing to set the product dosage and can be moved translationally relative to the casing in the conveying direction to deliver the product dosage set. If the conveying means comprises an axially movable piston for conveying the product, as in some preferred embodiments, the first conveying member can be a piston rod. In such embodiments, the first conveying member can, however in principle be a transfer member which first transfers a conveying movement by the second conveying member onto a piston rod.

In some preferred embodiments, the present invention comprises a display drum that can be rotated relative to the casing in a second threaded engagement, and moved translationally in and counter to the conveying direction. The display drum is in the second threaded engagement with the casing or with an intermediate structure connected to the casing. If the second threaded engagement is formed with an intermediate structure, the intermediate structure is connected to the casing such that it does not move relative to the casing either when the dosage is being set or during the conveying movement, or in both cases.

In accordance with the present invention, in some embodiments the device also comprises a coupler which couples the display drum to the second conveying member, secured against rotation, wherein a coupler engagement formed by the coupler for the rotationally secure coupling is automatically released when the device is activated for administering. Advantageously, the coupler engagement is released before the conveying stroke of the second conveying member begins. Because the second conveying member can be moved relative to the casing in and counter to the conveying direction, it forms a first spindle drive with the first conveying member and is coupled to the display drum via a releasable coupler engagement while the product dosage is being set, the thread pitches of the two spindle drives, i.e. the first spindle drive formed with the second conveying member and the second spindle drive formed with the display drum, can be simply varied with respect to each other over a broad range. Thus, the spindle drive formed with the display drum can exhibit a large thread pitch and the spindle drive formed with the second conveying member can exhibit a small thread pitch. A small conveying stroke can thus be combined with a large display stroke. The thread pitch in the second threaded engagement can be, for example, three, four or five times as large as the thread pitch in the first threaded engagement.

In some preferred embodiments, the threaded engagement between the conveying members is self-locking, which is advantageously achieved by making the pitch of the threads in the threaded engagement sufficiently small. Instead or additionally, a releasable locking engagement can prevent the second conveying member from performing an undesirable rotational movement during the conveying stroke. The angular distance of the rotational locking positions of such a locking engagement correspond to increasing or reducing the dosage by one settable unit.

In preferred embodiments, the coupler is tensed into the coupler engagement by a spring and, for this purpose, comprises a first coupler member and a second coupler member, as well as the spring which tenses the coupler members together in the coupler engagement. At least in embodiments in which the force required for performing the conveying stroke is applied manually, it may be preferred if the coupler engagement is released by the force to be applied for the conveying stroke. The activating force generating the conveying stroke is advantageously exerted in the conveying direction, and the spring tenses one of the coupler members in or counter to the conveying direction, into the coupler engagement with the other. The coupler engagement, i.e. the rotational block established by the coupler members, can be based purely on a frictional lock, but may be based on a positive lock or at least comprises a positive-lock connection between the coupler members. The coupler engagement may be released by a movement in the conveying direction which one of the coupler members performs relative to the other. Advantageously, one of the coupler members can be moved relative to the other in the conveying direction along the conveying axis, out of the coupler engagement.

For activating, the device comprises an activating element which, when activated, releases the coupler engagement. At least one of the display drum and the second conveying member, in some preferred embodiments, the display drum and the second conveying member as well, can be rotated relative to the activating element. The activating element is permanently connected to one of the two coupler members. It is connected to the relevant coupler member such that it cannot be moved in and counter to a direction in which the relevant coupler member is moved out of the coupler engagement. When activated, the activating element passes into contact against the other of the coupler members. The activating element and the other of the coupler members comprise low-friction contact areas for the contact, so that only small frictional forces oppose a relative rotation which may occur in the activating contact.

In some embodiments, the spring of the coupler is a mechanical spring. It advantageously acts as a pressure spring. Alternatively, however, it can for example also act as a tension spring, the spring force of which draws the coupler members into the coupler engagement. In one preferred embodiment as a pressure spring, it acts on the one hand against one of the coupler members and on the other hand against the second conveying member. As a pressure spring, it can alternatively also be formed as a pressurized gas spring, for example a pressurized air spring.

In some preferred embodiments, an equalizer or equalizing means is provided which is variable in length in the conveying direction and connects the second conveying member to the display drum, secured against rotation, when the coupler engagement exists. In some preferred embodiments, the equalizer comprises a spring arranged such that the length of the equalizer can only be reduced against a restoring elasticity force of the spring. The spring may be a mechanical spring, but could in principle also be a pneumatic spring. That which has been said with respect to the spring of the coupler applies similarly to the spring of the equalizer. The spring can be the spring described in connection with the coupler. In some embodiments, the spring serving to equalize the length can, however, be provided in addition to the spring of the coupler.

In some preferred embodiments, the equalizer comprises at least two equalizing structures which overlap each other in the conveying direction and are guided, secured against rotation, relative to each other. The at least two equalizing structures are rotationally guided directly on each other. When the coupler engagement exists, one of the equalizing structures is connected, secured against rotation, to the display drum, and the other is connected, secured against rotation, to the second conveying member. In some preferred embodiments, the equalizing is formed as a telescope. In such embodiments, the equalizing structures each form a telescopic section extending in the conveying direction. In advantageous embodiments, the spring of the equalizer is supported on one of the equalizing structures in the conveying direction and on the other of the equalizing structures counter to the conveying direction, such that the spring force tends to drive or move the equalizing structures apart. In some preferred embodiments, the equalizer only comprises exactly two equalizing structures which can be moved relative to each other in the conveying direction. Advantageously, the equalizing structures are rigid in their own right in the conveying direction, but could also themselves exhibit an elasticity in the conveying direction, such that a separate spring could be omitted. The equalizer could thus perfectly well be formed as bellows which can also simultaneously be one of the coupler members. The equalizer is advantageous in combination with the coupler. Further, it is advantageous for maintaining the rotationally secure connection between the display drum and the second conveying member, but is also advantageous in its own right alone.

In a preferred embodiment, the device comprises a guide for linearly guiding the first conveying member, secured against rotation, in the conveying direction. Advantageously, a torque cannot be transferred by such a first conveying member onto a conveying member, for example a piston, arranged subsequently in the conveying line.

in some preferred embodiments, a retainer or retaining means is provided which, when in engagement with the first conveying member, prevents the first conveying member from moving counter to the conveying direction. The retainer and the first conveying member—as far as its co-operation with the retaining means is concerned—can be formed in the way known from injection devices comprising gear rack arrangements. Thus, the first conveying member can, for example, be formed as a gear rack comprising at least one row of serrated teeth, with which an elastically bending retaining tongue of the retaining means engages, to prevent the first conveying member from moving counter to the conveying direction but allow it to move in the conveying direction.

In some preferred embodiments of the present invention, the administering device can be an injection device or apparatus, advantageously for subcutaneous administering by an injection needle or also for needle-free pressure injectors. The injection apparatus may be an injection pen. As already mentioned in connection with the retainer or retaining means, the device can be formed in the manner of a gear rack pen, wherein, however, the first conveying member is formed as a combined tooth-thread rack or at least comprises a corresponding section. Due to its simple design and therefore reasonable price, the device can also be provided as a disposable apparatus which is disposed of once the product container has been emptied.

DETAILED DESCRIPTION

Figure 1:
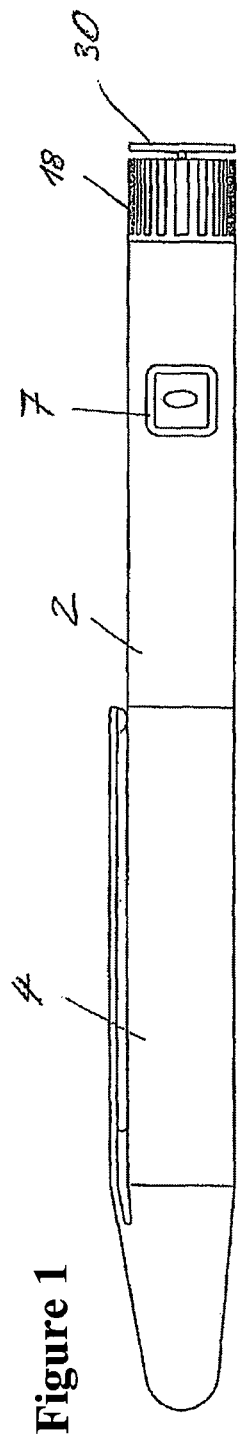
FIG. 1 depicts a device in accordance with the present invention and a dosage display in the state of a zero dosage setting.

FIG. 1 shows a device for administering or injecting a fluid product—for example insulin, an osteoporosis preparation, or a growth hormone—in doses. The device is formed as a slim injection pen. It comprises a casing, a proximal casing section 2 of which can be seen. A cap 4 covers a distal casing section. The device is depicted in an initial state which it assumes before a product dosage which is to be administered is set or after the product has been administered. A dosing member 18 for setting the product dosage and a dosage display comprising a window 7 can be seen. The window 7 is formed as an aperture in the casing section 2 and is covered by a transparent cover, for example a magnifier; in principle, the window 7 can also simply be just an aperture through which the dosage set by means of the dosing member 18 is legible on a dosage scale. In the initial state in FIG. 1, the dosage display displays the dosage "zero". A disc-shaped activating element 30 forms a proximal end of the device.

Figure 2:
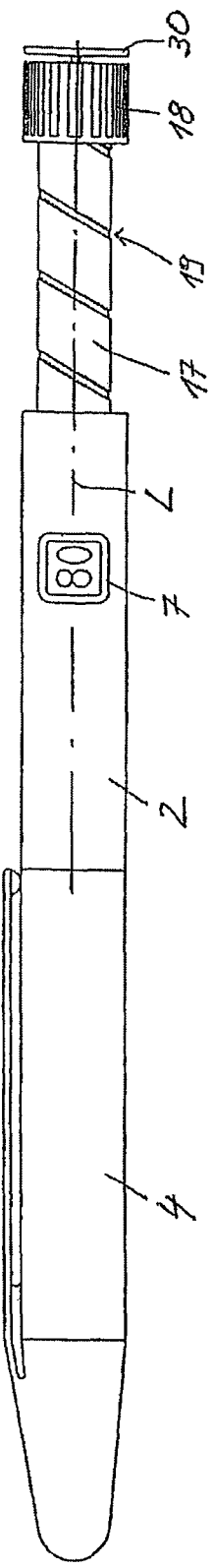
FIG. 2 shows the device of FIG. 1 in the state of a maximum dosage setting.

FIG. 2 shows the device in the same view as FIG. 1, but after a product dosage has been set which is the maximum product dosage which can be administered per injection using the device. As can be read on the dosage display, the maximum product dosage corresponds for example to 80 dosage units of the product. The dosing member 18 is formed as a rotating knob. The dosage is set by a rotational dosing movement of the dosing member 18. The rotational dosing movement rotates a display drum 17 out of the casing section 2 along a central longitudinal axis L of the device. The dosage scale is disposed, in a circumferential spiral, on the outer circumferential area of the display drum 17. The display drum 17 is provided, in a circumferential spiral around the central longitudinal axis L, with a thread 19 which is in threaded engagement with a corresponding inner thread of the casing section 2, such that the display drum 17 forms a spindle drive with the casing section 2. The pitch of the threaded engagement with respect to the central longitudinal axis L is large enough that self-locking cannot occur if the display drum 17 is pressed into the casing section 2 by pressure against the activating element 30.

Figure 3:
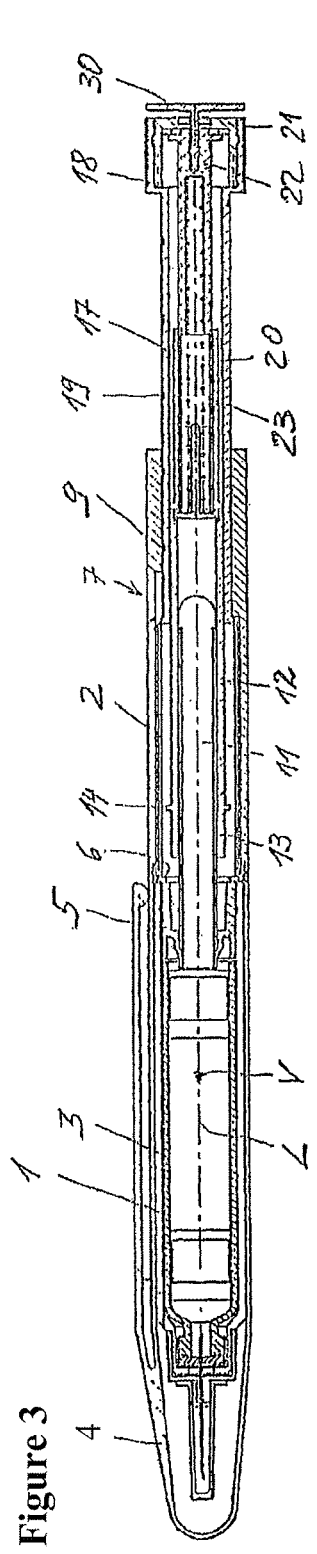
FIG. 3 shows the device of FIG. 1 in the state of the maximum dosage setting, in a longitudinal section.
Figure 4:
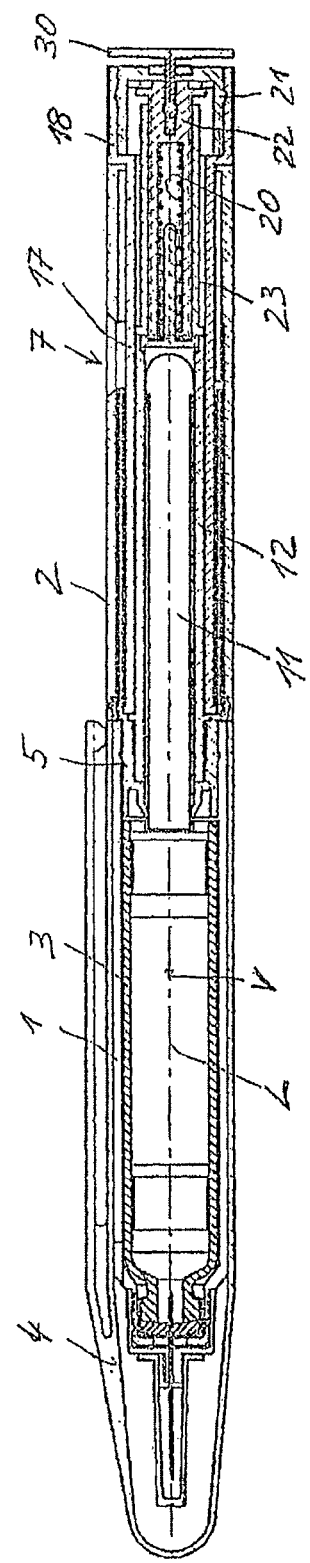
FIG. 4 shows the device in the state of the zero dosage setting, in the same sectional view as in FIG. 3.
Figure 5:
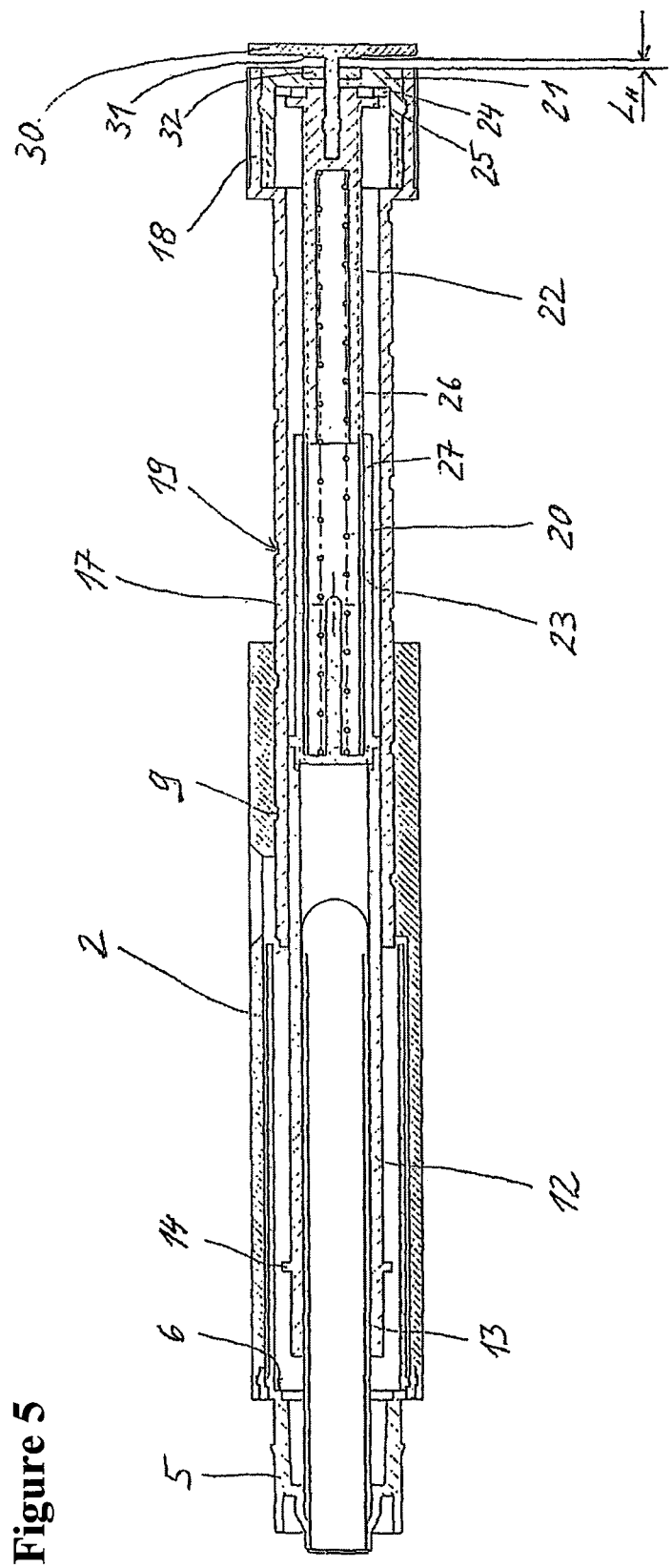
FIG. 5 shows a proximal portion of the device in the state of the maximum dosage setting, in the same longitudinal section as those of FIGS. 3 and 4.

FIG. 3 shows the device in the state in FIG. 2, i.e. in the state of the maximum dosage setting, in a longitudinal section which includes the central longitudinal axis L of the device. FIG. 4 shows the device in the state in FIG. 1, i.e. in the zero dosage setting, in the same longitudinal section. FIG. 5 shows—in the same longitudinal section, but enlarged—the proximal portion of the device in the state of the maximum dosage setting.

The distal casing section 1 and the proximal casing section 2 connected immovably to it form a casing or housing for the device. The distal casing section 1 forms a receptacle for a container 3 which is filled with the product and is formed by an ampoule such as is, for example, known for injection pens from diabetes therapy. A distal outlet of the ampoule is sealed by a septum. An injection cannula, arranged along the longitudinal axis L, protrudes through the septum. A piston is accommodated in the container 3 such that it can be moved along the longitudinal direction L in a conveying direction V towards the outlet. The longitudinal axis L also forms a conveying axis of the device and is also referred to as such in the following.

A piston rod drives the piston along the conveying axis L in the conveying direction V. The piston rod forms a first conveying member 11 of the injection operational mechanism or conveying means which also comprises the piston and a second conveying member 12 which drives the first conveying member 11. The first conveying member 11 is not visible in FIGS. 3, 4 and 5; the reference sign "11" indicates its installed location. The first conveying member 11 is in threaded engagement with the second conveying member 12, wherein the conveying axis L is the thread axis. The first conveying member 11 is also in engagement with a retainer or retaining means 5 connected to the casing section 2 such that it cannot be moved in or counter to the conveying direction V. The retainer 5 comprises two retaining tongues which engage with longitudinal grooves on the first conveying member 1 and block the first conveying member 1 from moving counter to the conveying direction V. For the retaining engagement with the two grooves, the first conveying member 1 is provided with a row of serrated teeth in each case. The co-operation between the first conveying member 1 and the retainer 5 corresponds to that of known gear rack pens. An example of such a pen is described in DE 102 32 411 A1, to which reference is made in this respect.

The first conveying member 11 also cannot be rotated relative to the casing section 2 around the conveying axis L, wherein a rotational block formed for this purpose blocks a rotational movement in both rotational directions in all operational states of the device. The retainer 5 can also simultaneously form the rotational block, or a rotational block can also be additionally provided.

The second conveying member 12 is sleeve-shaped, surrounds the first conveying member 1 and exhibits an inner thread 13 at its distal end which is in threaded engagement with an outer thread on the first conveying member 11. The inner thread 13 and the outer thread on the first conveying member 11 are fine threads having a correspondingly small thread pitch. The second conveying member 12 also similarly forms a conveying stopper 14 in its distal end region which projects radially outwardly and, in co-operation with a counter stopper 6 formed by the retainer 5, limits the conveying movement of the second conveying member 12 and therefore—because of the threaded engagement—also the conveying movement of the first conveying member 11 in the conveying direction V. The stopper 14 can be formed by a circumferential flange or a plurality of individual cams or as applicable also just one cam, if the counter stopper 6 encircles the conveying axis L.

In addition to the threaded engagement between the conveying members 11 and 12, another second threaded engagement is that formed between the display drum 17 and the casing section 2, i.e. between the outer thread 19 on the display drum 17 and an inner thread 9 on the casing section 2. The conveying axis L is also the threaded axis of the second threaded engagement. An annular gap remains between the second conveying member 12 and the casing section 2, which the display drum 17 enters in the second threaded engagement when the product is being delivered and leaves when the dosage is being set. As it enters and leaves, it slides over the outer surface area of the second conveying member 12 which apart from the stopper 14 is smooth. The display drum 17 is thus radially guided on both sides, on the one hand in the second threaded engagement 9, 19 and on the other hand by the second conveying member 12. Because the display drum 17 tightly surrounds the second conveying member 12, the pen can be kept very slim.

For setting the dosage, the second conveying member 12 is connected to the dosing member 18, secured against rotation, via a coupler. The dosing member 18 and the display drum 17 are in turn formed in one piece as a sleeve body, with the display drum 17 as an elongated distal sleeve section and the dosing member 18 as a relatively wider but axially shorter proximal end section.

The coupler comprises a first coupler member 21, a second coupler member 22 and a spring 20 which is formed as a spiral spring and acts as a pressure spring to press the second coupler member 22 into coupler engagement with the first coupler member 21. When engaged, the coupler members 21 and 22 are connected to each other in a positive lock, secured against rotation with respect to the conveying axis L. The first coupler member 21 is inserted into the sleeve section of the sleeve body which forms the dosing member 18, and is connected to the sleeve body both secured against rotation and such that it cannot be moved axially. The first coupler member 21 is formed in the shape of a cup, with a base at the proximal end and a wall which circumferentially protrudes up from the base in the distal direction. It thus seals the sleeve body at its proximal end. For the coupler engagement, the first coupler member 21 is fitted with coupler ribs, cams, grooves 24 or the like, and the second coupler member 22 is fitted with corresponding counter grooves, ribs or cams 25 or the like, which engage with each other to prevent one of the coupler members 21 and 22 from rotating relative to the other. In some embodiments, one pair of coupler elements consisting, for example, of a coupler rib 24 and a coupler groove 25 as the engaging elements is sufficient for the coupler engagement.

In a double function, the second coupler member 22 is also part of an equalizer or equalizing means which comprises the coupler member 22 as a first equalizing structure and a second equalizing structure 23 which co-operates with it. The spring 20 also fulfils a double function, on the one hand as a coupler spring of the coupler and on the other hand as an equalizing spring of the equalizer. The two equalizing structures 22 and 23 form a telescope, i.e. are telescopically coupled. They are linearly guided on each other, secured against rotation, in and counter to the conveying direction V along the conveying axis L, wherein the equalizing structure 22 forms an inner telescopic section and the equalizing structure 23 forms an outer telescopic section. For the rotational block, the equalizing structure 22 is provided with guiding elements 26 on its outer surface area, and the equalizing structure 23 is provided with guiding counter elements 27 on its inner surface area. The guiding elements 26 and 27 are formed in the manner of a groove and spring guide. In principle, the guide could also be formed by just one guiding element and one guiding counter element.

As shown in FIGS. 3 to 5, the two equalizing structures 22 and 23 overlap each other almost completely in the state of the zero dosage setting, while the axial overlap is minimal in the state of the maximum dosage setting and still ensures the rotationally secured connection between the display drum 17 and the dosing member 18 on the one hand and the second conveying member 12 on the other. The equalizing structure 23 is cup-shaped, with a base at the distal end and a sleeve wall which circumferentially protrudes up from the base in the proximal direction. The spring 20 is supported in the conveying direction V on the base of the equalizing structure 23. An axial guide for the spring 20 also protrudes centrally up from the base. The spring 20 presses the equalizing structure 23 in the conveying direction V until it abuts against the second conveying member 12. The second conveying member 12 and the equalizing structure 23 are also in a rotationally secured engagement with each other with respect to the conveying axis L. For the rotationally secured engagement, the second conveying member 12 comprises axially short engaging elements on an inner surface area of its proximal end which are in the rotationally secured engagement with counter elements formed on the outer surface area of the equalizing structure 23. The equalizing structure 23 is a separate component in this exemplary embodiment, but can alternatively be formed in one piece with the second conveying member 12. Forming it as a separate component may be advantageous for production reasons.

The activating element 30 forms a disc-shaped closing end of the device. A pin-shaped connecting section protrudes in the conveying direction V from the disc-shaped structure, through the base of the first coupler member 21, into the interior of the dosing member 18, where it is anchored in a base section of the second coupler member 22, which is similarly cup-shaped, such that the coupler member 22 and the activating element 30 cannot be moved relative to each other in or counter to the conveying direction V. In some preferred embodiments, they can be rotated relative to each other around the conveying axis L; in principle, however, they can also be connected to each other, secured against rotation. The activating element 30 can be moved, together with the second coupler member 22, in the conveying direction V relative to the first coupler member 21, against the restoring elasticity force of the spring 20. It can also be rotated around the conveying axis L at least relative to the first coupler member 21.

As can be seen most clearly in FIG. 5, a clearance "LH" remains axially between the activating element 30 and the first coupler member 21, apart from the connecting section of the activating element 30. The distance LH is between contact areas of the activating element 30 and coupler member 21 which axially oppose each other. The contact area of the activating element 30 is indicated as 31 and is formed centrally around the connecting section of the activating element 30 as a raised area protruding up in the distal direction. To form the counter contact area, a contact element 32 is incorporated into the coupler member 21, complementarily to the contact area 31. The contact area 31 and the counter area of the contact element 32 are formed to be low-friction and may be, for example, made of Teflon.

How the device functions when the dosage is being set and administered is described below on the basis of FIGS. 3 and 4, wherein reference should also be made to FIG. 5.

The device reaches the user in the state of the zero dosage setting, as shown in FIG. 4. The full container 3 is inserted in the receptacle of the distal casing section 1. For a first injection, the user takes off the cap 4 and removes a needle protection which surrounds the injection needle.

Before the desired dosage has been set, the cap 4 can be re-attached for safety reasons. To set the dosage, the user holds the device in the region of the casing or, if the cap 4 is attached, in the region of the casing section 2 and rotates the dosing member 18 until the desired dosage has been set. Due to the rotational dosing movement, the drum 17—in the second threaded engagement—moves in the proximal direction, out of the casing section 2. The dosage corresponding to the current dosing position is legible in the window 7. The rotational dosing movement is performed in discrete steps between locking positions, wherein a distinct clicking sound can be perceived during each locking process. The maximum dosage setting is determined by a stopper on the display drum 17 and a counter stopper on the casing section 2. Between the two extreme settings of the zero dosage and the maximum dosage, the dosing member 18 and together with it the display drum 17 can be rotated in both rotational directions from one locking position to the next, as desired, such that it is easily possible to correct a dosage.

While the display drum 17 and the dosing member 18 are moved out, the second coupler member 22 is held permanently in coupler engagement with the first coupler member 21 by the spring 20. During the rotational dosing movement, the coupler member 22 is also permanently in rotationally secured engagement with the equalizing structure 23, which for its part is held in rotationally secured engagement with the second conveying member 12. The rotational portion of the rotational dosing movement is thus transferred onto the second conveying member 12. Since the first conveying member 11 cannot be rotated relative to the casing and is also prevented from moving counter to the conveying direction V by the retaining means 5, the second conveying member 12—in threaded engagement with the first conveying member 11—is screwed counter to the conveying direction V, relative to the first conveying member 11. During this dosing stroke which the second conveying member 12 performs relative to the first conveying member 11, the axial distance between the stopper 14 and the counter stopper 6 is changed. This axial distance corresponds to the length of the dosing stroke and correspondingly also to the length of the conveying stroke.

Since the thread pitch in the second threaded engagement (which may be referred to or thought of as the engagement of threads 9, 19) is larger than in the threaded engagement between the conveying members 11 and 12—in the embodied apparatus, slightly over four times as large—the stroke completed by the display drum 17 when the dosage is being set is longer, over the same rotational angle, in accordance with the ratio between the pitches. The dosage values are correspondingly large and sufficiently spaced from each other on the dosage scale.

The axial dosing stroke of the display drum 17 and dosing member 18, i.e. the translational portion of the dosing movement, is longer than the dosing stroke of the second conveying member 12. The equalizer, comprising structures 20, 22 and 23, equalizes the difference in length, such that the rotationally secured connection between the display drum 17 and the dosing member 18 on the one hand and the second conveying member 12 on the other always exists, in the coupler engagement, between the extreme settings—the zero dosage setting and the maximum dosage setting—limited by stoppers.

Once the desired dosage, for example the maximum dosage which in the exemplary embodiment measures 80 units (FIG. 2), has been set, the user takes off the cap 4, if it was still attached for safety reasons, injects the injection needle through the skin at the desired injection point and thus positions the needle tip in the subcutaneous tissue.

While the injection needle is positioned subcutaneously, the user holds the device with one hand in the region of the casing and presses his/her thumb against the activating element 30 in the conveying direction V. In a first phase of the activating stroke, the pressure moves the second coupler member 22 in the conveying direction V relative to the first coupler member 21, against the pressure of the spring 20, out of the coupler engagement. The axial length of the engaging elements 24 and 25 mediating the coupler engagement is set such that the coupler engagement is released when the activating element 30 has traveled the idle stroke LH relative to the coupler member 21. In the event of further pressure on the activating element 30, the activating element 30 presses against the coupler member 22 via the contact element 32, such that in the second phase of the activating stroke, the display drum 17—in the second threaded engagement—is screwed into the casing section 2, wherein the second coupler member 22 moves telescopically in the equalizing structure 23 up to an axial stopper which in the example embodiment is formed by the base of the equalizing structure 23. As soon as the coupler member 22 abuts against the equalizing structure 23, further pressure on the activating element 30 causes the second conveying member 22 to then be slaved in the final phase of the activating stroke due to the equalizing structure 23 pressing it, and to perform the conveying stroke. The conveying stroke is limited by the pair of stoppers 6, 14. The activating stroke is functionally divided into phases, but is advantageously performed continuously.

Once the conveying stroke has been completely performed, the pressure is taken off the activating element 30, such that the spring 20 presses the coupler member 22 back into coupler engagement with the coupler member 21. Once the injection needle has been drawn out of the tissue, the cap 4 is re-attached. The device is then back in the state in FIG. 4, only without the needle protection cap which is only present before the device is used for the first time. The device is stored in this state until the next injection.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering a product dose, the device comprising a display drum for displaying the product dose, a housing, a first conveying member moveable relative to the housing in a conveying direction, a second conveying member moveable relative to the housing in and counter to the conveying direction, the second conveying member in a first threaded engagement with the first conveying member while being rotationally movable relative to the housing and the first conveying member and being movable relative to the first conveying member counter to the conveying direction, a translational metering apparatus by which the product dose can be adjusted and which comprises the display drum, the display drum being rotationally movable relative to the housing while being translationally movable in and counter to the conveying direction in a second threaded engagement, a thread pitch of the second threaded engagement larger than a thread pitch of the first threaded engagement so that an axial dosing stroke of the display drum is longer than an axial dosing stroke of the second conveying member, a coupling element which interconnects the second conveying member and the display drum in a torsion-resistant manner in a coupling engagement which is releasable by actuating the device for administering, and an equalizer comprising a structure having a variable length for equalizing a difference in length of the axial dosing stroke of the display drum and the axial dosing stroke of the second conveying member to maintain the interconnection between the second conveying member and the display drum, secured against relative rotation, when the coupling engagement exists.

2. The device for administering according to claim 1, wherein the coupling element comprises a first coupler member, a second coupler member and a spring which urges the second coupler member into a coupler engagement with the first coupler member.

3. The device for administering according to claim 2, wherein the equalizer structure comprises at least two equalizing structures which overlap each other in the conveying direction and are guided, secured against rotation, relative to each other, and wherein when the coupler engagement exists, one of the equalizing structures is connected, secured against rotation, to the display drum, and the other is connected, secured against rotation, to the second conveying member, wherein the second coupler member forms one of the equalizing structures.

4. The device for administering according to claim 1, wherein the equalizer forms a telescope.

5. The device for administering according to claim 1, wherein the equalizer structure comprises at least two equalizing structures which overlap each other in the conveying direction and are guided, secured against rotation, relative to each other, and wherein when the coupling engagement exists, one of the equalizing structures is connected, secured against rotation, to the display drum and the other is connected, secured against rotation, to the second conveying member.

6. The device for administering according to claim 5, further comprising a spring which acts on one of the equalizing structures in the conveying direction and acts on the other of the equalizing structures counter to the conveying direction.

7. An administering device comprising a display drum, the device comprising:
   a) a casing comprising a receptacle for a product to be administered;
   b) a first conveying member moveable in a conveying direction relative to the casing to convey the product;
   c) a second conveying member moveable in and counter to the conveying direction relative to the casing in a first threaded engagement with the first conveying member, rotationally relative to the casing and the first conveying member, and translationally counter to the conveying direction relative to the first conveying member;
   d) dosing means from which a product dosage can be set and which comprises the display drum for displaying the product dosage, wherein said display drum can be moved in a second threaded engagement, rotationally relative to the casing and translationally in and counter to the conveying direction; and
   e) a coupler comprising a first coupler member and a second coupler member and a spring that urges the second coupler member into a coupler engagement with the first coupler member such that the coupler engagement connects the second conveying member and the display drum to each other in a the coupler engagement, secured against relative rotation; and
   f) an equalizer arranged within an interior of the display drum and comprising first and second telescopically arranged sleeves such that that the equalizer is variable in length in the conveying direction against a spring force of the spring arranged between the first and second sleeves, the equalizer sleeves connecting the second conveying member to the display drum, secured against relative rotation when the coupler engagement exists, wherein one of the first and second sleeves is formed by the second coupler member;
   g) wherein the coupler engagement is released by activating the administering device.

8. The administering device according to claim 7, wherein the display drum is one of connected to one of the coupler members, secured against relative rotation, or forms one of the coupler members.

9. The administering device according to claim 7, wherein the spring urges the second coupler member into the coupler engagement either in or counter to the conveying direction.

10. The administering device according to claim 7, wherein the second conveying member and the second coupler member are moveable translationally along a common axis.

11. The administering device according to claim 7, wherein the coupler engagement is a positive-lock engagement between the two coupler members via an engagement between complementary releasable locking structures arranged at facing ends of each of the coupler members.

12. The administering device according to claim 7, further comprising an activating element for the second conveying member and at least one of the display drum and the second conveying member can be rotated relative to the activating element.

13. The administering device according to claim 7, further comprising an activating element for the second conveying member and at least one of the display drum and the second conveying member can be rotated relative to the activating element, wherein the activating element for activating the second conveying member can be moved relative to at least one of the casing and the first coupler member and is coupled to the second coupler member such that it moves the second coupler member out of the coupler engagement during a movement which is generated by activating the second conveying member and is in the conveying direction.

14. The administering device according to claim 13, wherein after the coupler engagement has been released, the activating element passes into an engagement in which it slaves the display drum when moved further.

15. The administering device according to claim 14, wherein the activating element passes into engagement with the display drum after the coupler engagement has been released.

16. The administering device according to claim 13, wherein once the coupler engagement has been released, the activating element passes into an active connection with the second conveying member via the second coupler member, in which it slaves the second conveying member when moved further.

17. The administering device according to claim 7, wherein a length of the equalizer can be reduced against the spring force of the spring.

18. The administering device according to claim 7, wherein the equalizer sleeves overlap each other in the conveying direction and are guided, secured against rotation, relative to each other, and in that when the coupler engagement exists, one of the equalizing sleeves is connected, secured against rotation, to the display drum, and the other is connected, secured against rotation, to the second conveying member, wherein the spring acts on the equalizer and the coupler.

19. The administering device according to claim 7, further comprising a guide by which the first conveying member is guided along a conveying axis pointing in the conveying direction such that it cannot be rotated relative to the casing with respect to both rotational directions.

20. The administering device according to claim 7, further comprising a retaining means which, when in engagement with the first conveying member, prevents the first conveying member from moving counter to the conveying direction.

21. The administering device according to claim 7, wherein the first conveying member is a piston rod.

22. An administering device comprising a display drum, the device comprising:
   a) a casing comprising a receptacle for a product to be administered;
   b) a first conveying member moveable in a conveying direction relative to the casing to convey the product;
   c) a second conveying member moveable in and counter to the conveying direction relative to the casing in a first threaded engagement with the first conveying member, rotationally relative to the casing and the first conveying member, and translationally counter to the conveying direction relative to the first conveying member, the first threaded engagement comprising a first thread pitch;
   d) a dosing mechanism for setting a product dosage comprising the display drum for displaying the product dosage, wherein said display drum can be moved in a second threaded engagement with the casing, rotationally relative to the casing and translationally in and counter to the conveying direction, the second threaded engagement comprising a second thread pitch larger than the first thread pitch;
   e) a coupler which connects the second conveying member and the display drum to each other in a coupler engagement, secured against relative rotation, wherein the coupler engagement is released by activating the administering device; and
   f) an equalizer which is variable in length in the conveying for equalizing a difference in length of an axial dosing stroke of the display drum compared to an axial dosing stroke of the second conveying member due to the larger second thread pitch, the equalizer connecting the second conveying member to the display drum, secured against relative rotation, when the coupler engagement exists.

* * * * *